US007706869B2

(12) United States Patent
Cao et al.

(10) Patent No.: US 7,706,869 B2
(45) Date of Patent: Apr. 27, 2010

(54) AUTOMATED TEMPLATE GENERATION ALGORITHM FOR IMPLANTABLE DEVICE

(75) Inventors: Jian Cao, Shoreview, MN (US); Jeffrey M. Gillberg, Coon Rapids, MN (US)

(73) Assignee: Medtronic, Inc., Minneapolis, MN (US)

( * ) Notice: Subject to any disclaimer, the term of this patent is extended or adjusted under 35 U.S.C. 154(b) by 135 days.

(21) Appl. No.: 10/826,618

(22) Filed: Apr. 16, 2004

(65) Prior Publication Data

US 2005/0234359 A1 Oct. 20, 2005

(51) Int. Cl.
*A61N 1/365* (2006.01)
(52) U.S. Cl. ....................................................... 600/518
(58) Field of Classification Search .................. 600/518
See application file for complete search history.

(56) References Cited

U.S. PATENT DOCUMENTS

| 4,726,380 A | 2/1988 | Vollmann et al. ..... 128/419 PG |
| 4,830,006 A | 5/1989 | Haluska et al. ....... 128/419 PG |
| 4,880,005 A | 11/1989 | Pless et al. ............ 128/419 PG |
| 5,117,824 A | 6/1992 | Keimel et al. .......... 128/419 D |
| 5,545,186 A | 8/1996 | Olson et al. ..................... 607/14 |
| 5,755,736 A | 5/1998 | Gillberg et al. ................. 607/4 |
| 5,991,656 A | 11/1999 | Olson et al. ..................... 607/4 |
| 6,312,388 B1 | 11/2001 | Marcovecchio et al. |
| 6,393,316 B1 | 5/2002 | Gillberg et al. ............. 600/515 |
| 6,687,540 B2 * | 2/2004 | Marcovecchio ................ 607/5 |
| 6,745,068 B2 | 6/2004 | Koyrakh et al. ............. 600/515 |
| 2002/0008791 A1 | 1/2002 | Okamori et al. ................ 349/5 |
| 2002/0183637 A1 | 12/2002 | Kim et al. .................... 600/510 |
| 2002/0183640 A1 | 12/2002 | Bjorling ...................... 600/517 |
| 2002/0193695 A1 | 12/2002 | Koyrakh et al. ............. 600/510 |
| 2004/0116972 A1 * | 6/2004 | Marcovecchio .............. 607/14 |

OTHER PUBLICATIONS

Anderson, MH et al., "Performance of Basic Ventricular Tachycardia Detection Algorithms in Implantable Cardioverter Defibrillators: Implications for Device Progrannning," *PACE*, vol. 20, p. 2975-2983 (1997).

Duru, F. et al., "Morphology Discriminator Feature for Enhanced Ventricular Tachycardia Discrimination implantable Cardioverter Defibrillators,"*PACE*, vol. 23, p. 1365-1374 (2000).

(Continued)

*Primary Examiner*—George R Evanisko
*Assistant Examiner*—Michael Kahelin
(74) *Attorney, Agent, or Firm*—Stephen W. Bauer; Michael C. Soldner

(57) ABSTRACT

A method and device for generating a template that includes identifying events of a plurality of sensed events having predetermined characteristics as first selected events and generating the template from the first selected events. Events of the plurality of events having the predetermined characteristics are identified as second selected events, and a determination is made as to whether the template is valid in response to the second selected events. The template is updated from the second selected events in response to the template not being valid.

19 Claims, 8 Drawing Sheets

OTHER PUBLICATIONS

Gillberg, J.M. et al., "Stability of Far-Field Electrogram Morphology During Baseline Rhythm in Patients with Implantable Cardioverter Defibrillators," *PACE*, vol. 23, p. 606 (abstract) (2000).

Gold, M.R. et al., "A New Defibrillator Discrimination Algorithm Utilizing Electrogram Morphology Analysis," *PACE*, vol. 22, p. 179-182 (1999).

Olson et al., "Onset and Stability for Ventricular Tachyarrhythmia Detection in an Implantable Pacer-Cardioverter-Defibrillator," *Computers in Cardiology*, IEEE Computer Society Press, p. 167-170 (Oct. 7-10, 1986).

Trivedi, A. et al., "Changes in Ventricular Electrogram Morphology Following ICD Insertion," *PACE*, vol. 23, p. 629 (abstract) (2000).

U.S. Appl. No. 10/826,512, filed Apr. 16, 2004, to Jian Cao et al, entitled "Automated Template Generation Algorithm for Implantable Device".

\* cited by examiner

AUTOMATED TEMPLATE GENERATION ALGORITHM FOR IMPLANTABLE DEVICE

CROSS-REFERENCE TO RELATED APPLICATION

Cross-reference is hereby made to commonly assigned U.S. application Ser. No. 10/826,512 filed concurrently herewith, , entitled "AUTOMATED TEMPLATE GENERATION ALGORITHM FOR IMPLANTABLE DEVICE", to Cao et al., incorporated herein by reference in its entirety.

FIELD OF THE INVENTION

The present invention relates generally to implantable medical devices, and in particular, the present invention relates to automatic creation of a template for EGM morphology measurements in an implantable medical device.

BACKGROUND OF THE INVENTION

In the medical fields of cardiology and electrophysiology, many tools are used to assess the condition and function of a patient's heart, including the observed frequency, polarity and amplitudes of the PQRST complex associated with a heart cycle. Such tools include classic external ECG systems for displaying and recording the characteristic lead ECG signals from skin electrodes placed on the patient's chest and limbs, ambulatory ECG Holter monitors for continuously recording the ECG or segments thereof from a more limited set of skin electrodes for a period of time, and more recently developed completely implantable cardiac monitors or cardiac pacemakers and pacemaker/cardioverter/defibrillators (PCDs) or implantable cardioverter/defibrillators (ICDs) having the capability of recording EGM segments or data derived from atrial and ventricular EGMS (A-EGMs and V-EGMs) for telemetry out to an external programmer for external storage and display.

One of the problems addressed in the design of implantable PCDs or ICDs is the avoidance of unnecessary electrical shocks delivered to a patient's heart in response to rapid heart rates caused by exercise (sinus tachycardia) or by atrial fibrillation. Such rhythms are known collectively as supraventricular tachycardias (SVTs). Studies have shown that SVTs may occur in up to 30% of ICD patients. While ICDs are generally effective at identifying ventricular tachycardia events, the ICD can occasionally deliver a therapy to treat what is detected as being a ventricular tachycardia when in fact the source of the event is related to a supraventricular tachycardia event. Since delivery of the treatment is painful and disconcerting to the patient, deficiencies in distinguishing ventricular tachycardia events from supraventricular tachycardia events tends to be problematic, making the reduction of the incidences of inappropriate treatment highly desirable.

One approach to the problem of distinguishing between normal QRS complexes present during SVTs from those indicative of a VT is to study the morphology of the QRS complex and discriminate normal heart beats from abnormal ones based on the similarity of the signal to a sample waveform recorded from the normal heartbeat, typically referred to as a template. Since a normal QRS complex, or slow rate rhythm, is generally narrower than the QRS complex during VT, or fast rate rhythm, one of the existing methods to discriminate between VT and normal EGM waveforms is based on the properly measured width of the QRS complex. By creating the template based on information sensed from supraventricular rhythm complexes, the ICD is able to compare cardiac complexes sensed during tachycardia episodes against the supraventricular rhythm template. Based on the results of the comparison, the ICD is able to classify the tachycardia episodes as being either a VT complex or a SVT complex, and delivers therapy according to the classification.

In theory, the shape of the QRS complex in the EGM signal during SVT will not change significantly in most patients, because ventricular depolarizations are caused by normal HIS-Purkinje conduction from the atrium to the ventricle. If high ventricular rates are due to a ventricular tachycardia (VT), one can expect a very different morphology of the electrogram (EGM) signal of the ventricular depolarization (QRS complex) because of a different pattern of electrical activity of the heart during VT. However, in certain instances, such as during the electrode/tissue maturation process, or when the patient begins taking new or additional medications, develops a myocardial infarction, or experiences other physiological changes causing the electrical tissue of the patient to change, the morphology of the normal heart rhythm of the patient may change from that originally used as a basis for creating the template. As a result, since deviation from the "normal" heart rhythm of the patient occurs, the template begins to become corrupted, no longer being representative of the patient's current normal heart rhythm and therefore causing the number of inappropriately delivered therapies to increase.

In addition to reducing delivery of inappropriate therapy, another major consideration to be taken into account in the development of the ICD is the limited battery power of the ICD that is available. Since the batteries supplied in the ICD cannot be replaced after initial implantation of the device without surgical procedures, the entire ICD must typically be surgically replaced once the batteries become depleted, making it very desirable to conserve battery power of the ICD. As a result, one of the ways to conserve battery power is to reduce the current drain by reducing the complexity of the signal processing that must be performed by the ICD, limiting the available solutions to reduction of inappropriate therapy delivery. Accordingly, what is needed is a method for reducing the instances of inappropriate therapy delivery that maximizes conservation of the battery power of the device.

BRIEF DESCRIPTION OF THE DRAWINGS

Aspects and features of the present invention will be readily appreciated as the same becomes better understood by reference to the following detailed description when considered in connection with the accompanying drawings, wherein.

DETAILED DESCRIPTION OF THE INVENTION

Figure 1:
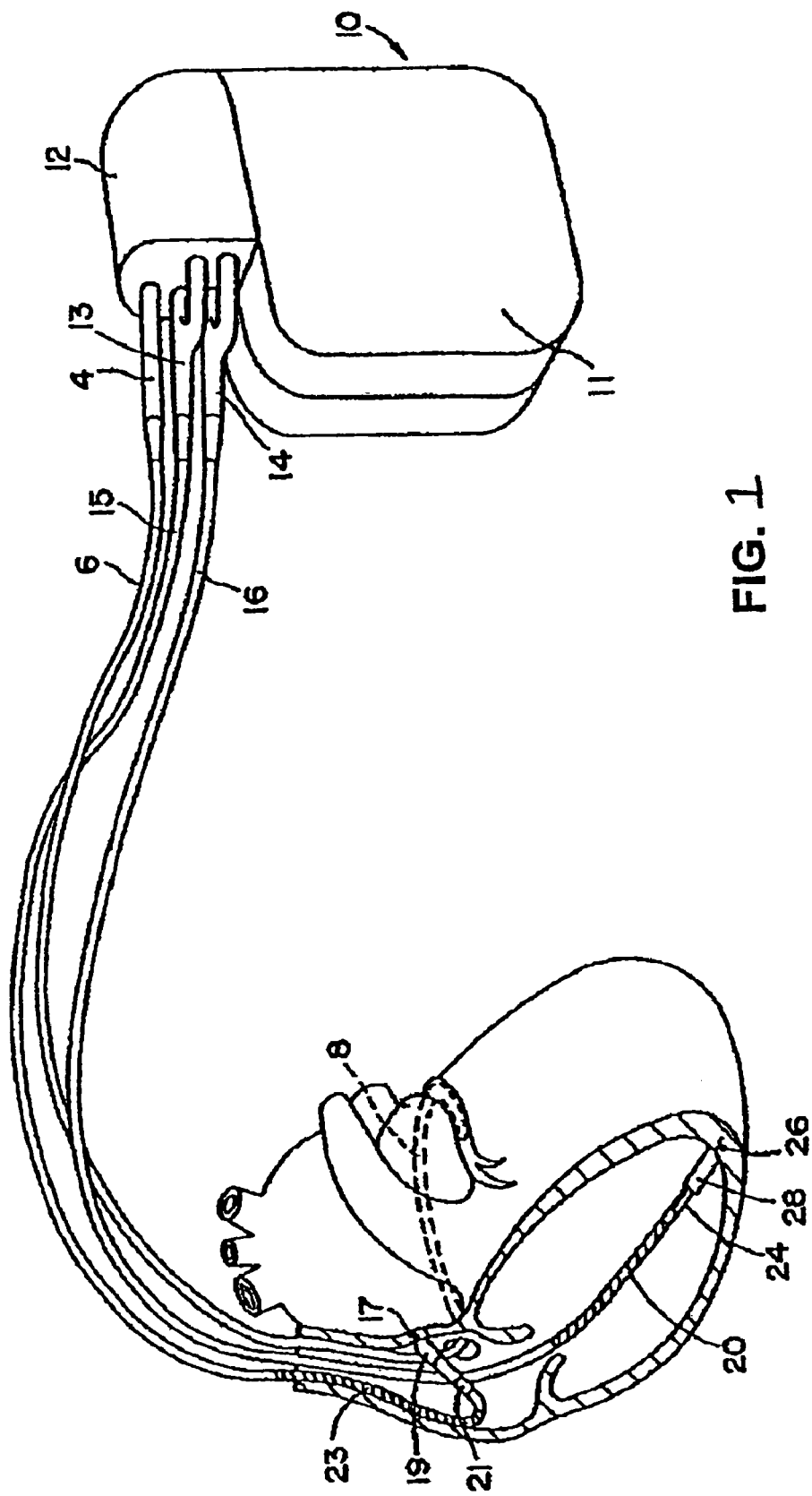
FIG. 1 is a schematic diagram of an implantable medical device of a type in which the present invention may usefully be practiced.

FIG. 1 is a schematic diagram of an implantable medical device of a type in which the present invention may usefully be practiced. As illustrated in FIG. 1, an implantable medical device 10, such as an implantable cardioverter defibrillator (ICD), for example, is coupled to a heart of a patient by way of one or more leads 6, 15, and 16. A connector block 12 receives the proximal end of a right ventricular lead 16, a right atrial lead 15 and a coronary sinus lead 6, used for positioning electrodes for sensing and stimulation in three or four heart chambers. In FIG. 1, right ventricular lead 16 is positioned such that its distal end is in the right ventricle for sensing right ventricular cardiac signals and delivering pacing or shocking pulses in the right ventricle. For these purposes, right ventricular lead 16 is equipped with a ring electrode 24, an extendable helix electrode 26 mounted retractably within an electrode head 28, and a coil electrode 20, each of which are connected to an insulated conductor within the body of lead 16. The proximal end of the insulated conductors are coupled to corresponding connectors carried by bifurcated connector 14 at the proximal end of lead 16 for providing electrical connection to the device 10.

The right atrial lead 15 is positioned such that its distal end is in the vicinity of the right atrium and the superior vena cava. Lead 15 is equipped with a ring electrode 21 and an extendable helix electrode 17, mounted retractably within electrode head 19, for sensing and pacing in the right atrium. Lead 15 is further equipped with a coil electrode 23 for delivering high-energy shock therapy. The ring electrode 21, the helix electrode 17 and the coil electrode 23 are each connected to an insulated conductor with the body of the right atrial lead 15. Each insulated conductor is coupled at its proximal end to a connector carried by bifurcated connector 13.

The coronary sinus lead 6 is advanced within the vasculature of the left side of the heart via the coronary sinus and great cardiac vein. The coronary sinus lead 6 is shown in the embodiment of FIG. 1 as having a defibrillation coil electrode 8 that may be used in combination with either the coil electrode 20 or the coil electrode 23 for delivering electrical shocks for cardioversion and defibrillation therapies. In other embodiments, coronary sinus lead 6 may also be equipped with a distal tip electrode and ring electrode for pacing and sensing functions in the left chambers of the heart. The coil electrode 8 is coupled to an insulated conductor within the body of lead 6, which provides connection to the proximal connector 4.

The electrodes 17 and 21 or 24 and 26 may be used as true bipolar pairs, commonly referred to as a "tip-to-ring" configuration. Further, electrode 17 and coil electrode 20 or electrode 24 and coil electrode 23 may be used as integrated bipolar pairs, commonly referred to as a "tip-to-coil" configuration. In some cases, electrodes 17, 21, 24, and 26 may be used individually in a unipolar configuration with the device housing 11 serving as the indifferent electrode, commonly referred to as the "can" or "case" electrode.

The device housing 11 may also serve as a subcutaneous defibrillation electrode in combination with one or more of the defibrillation coil electrodes 8, 20 or 23 for defibrillation of the atria or ventricles. It is recognized that alternate lead systems may be substituted for the three lead system illustrated in FIG. 1. While a particular multi-chamber ICD and lead system is illustrated in FIG. 1, methodologies included in the present invention may adapted for use with any single chamber, dual chamber, or multi-chamber ICD or pacemaker system, or other cardiac monitoring device.

Figure 2:
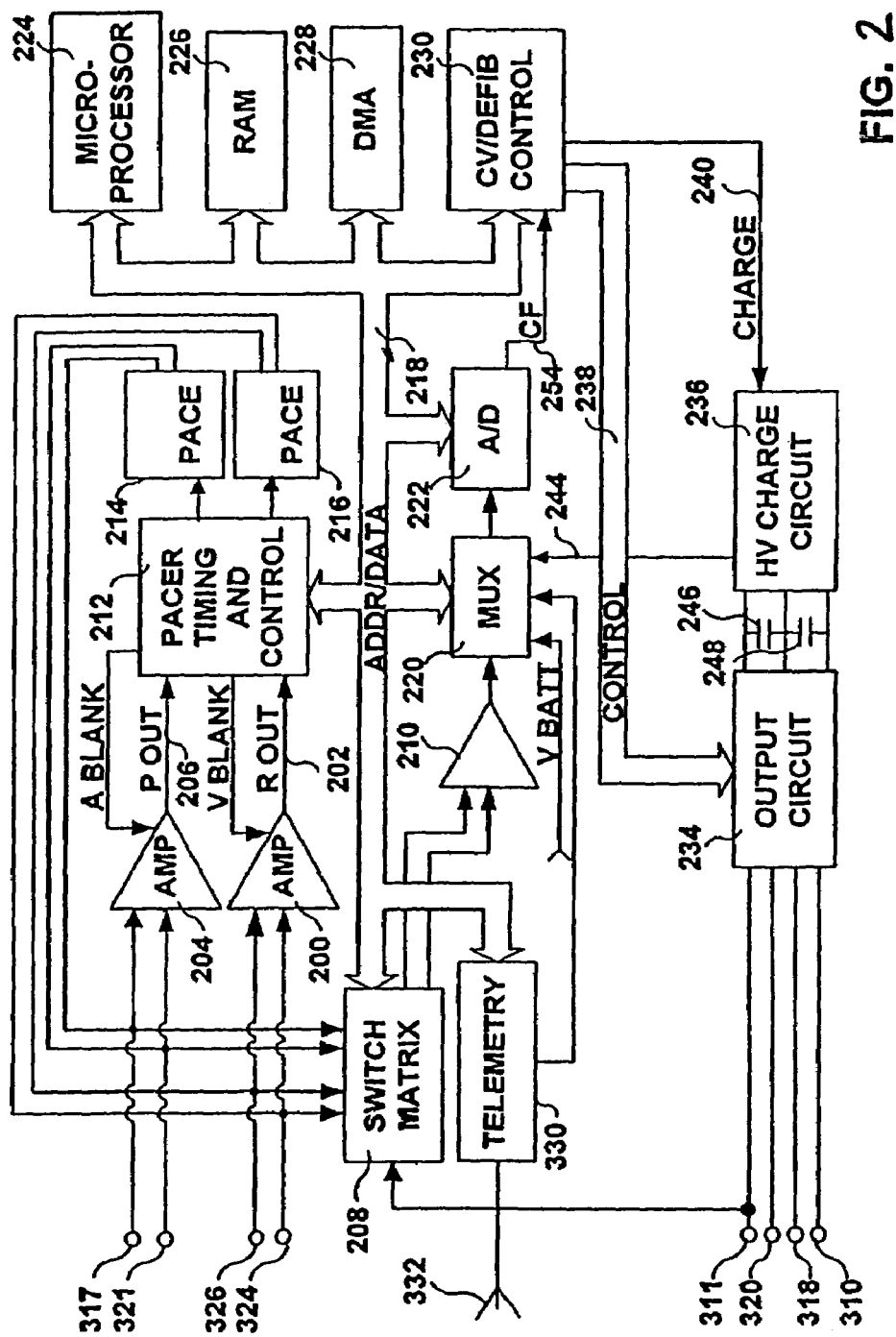
FIG. 2 is a functional schematic diagram of an implantable medical device of the type illustrated in FIG. 1, in which the present invention may usefully be practiced.

FIG. 2 is a functional schematic diagram of an implantable medical device of the type illustrated in FIG. 1, in which the present invention may usefully be practiced. This diagram should be taken as exemplary of the type of device with which the invention may be embodied and not as limiting. The disclosed embodiment shown in FIG. 2 is a microprocessor-controlled device, but the methods of the present invention may also be practiced with other types of devices such as those employing dedicated digital circuitry.

With regard to the electrode system illustrated in FIG. 1, device 10 is provided with a number of connection terminals for achieving electrical connection to the leads 6, 15, and 16 and their respective electrodes. A connection terminal 311 provides electrical connection to the housing 11 for use as the indifferent electrode during unipolar stimulation or sensing. The connection terminals 320, 310, and 318 provide electrical connection to coil electrodes 20, 8 and 23 respectively. Each of these connection terminals 311, 320, 310, and 318 are coupled to the high voltage output circuit 234 to facilitate the delivery of high energy shocking pulses to the heart using one or more of the coil electrodes 8, 20, and 23 and optionally the housing 11.

The connection terminals 317 and 321 provide electrical connection to the helix electrode 17 and the ring electrode 21 positioned in the right atrium. The connection terminals 317 and 321 are further coupled to an atrial sense amplifier 204 for sensing atrial signals such as P-waves. The connection terminals 326 and 324 provide electrical connection to the helix electrode 26 and the ring electrode 24 positioned in the right ventricle. The connection terminals 326 and 324 are further coupled to a ventricular sense amplifier 200 for sensing ventricular signals.

The atrial sense amplifier 204 and the ventricular sense amplifier 200 preferably take the form of automatic threshold or gain controlled amplifiers with adjustable sensitivity. The general operation of the ventricular sense amplifier 200 and the atrial sense amplifier 204 may correspond to that disclosed in U.S. Pat. No. 5,117,824, by Keimel, et al., incorporated herein by reference in its entirety. Whenever a signal received by atrial sense amplifier 204 exceeds an atrial sensitivity, a signal is generated on the P-out signal line 206. Whenever a signal received by the ventricular sense amplifier 200 exceeds a ventricular sensitivity, a signal is generated on the R-out signal line 202.

Switch matrix 208 is used to select which of the available electrodes are coupled to a wide band amplifier 210 for use in digital signal analysis. Selection of the electrodes is controlled by the microprocessor 224 via data/address bus 218. The selected electrode configuration may be varied as desired for the various sensing, pacing, cardioversion and defibrillation functions of the device 10.

Signals from the electrodes selected for coupling to bandpass amplifier 210 are provided to multiplexer 220, and thereafter converted to multi-bit digital signals by A/D converter 222, for storage in random access memory 226 under control of direct memory access circuit 228. Microprocessor 224 may employ digital signal analysis techniques to characterize the digitized signals stored in random access memory 226 to recognize and classify the patient's heart rhythm employing any of the numerous signal processing methodologies known in the art. An exemplary tachyarrhythmia recognition system is described in U.S. Pat. No. 5,545,186 issued to Olson et al, incorporated herein by reference in its entirety.

The telemetry circuit 330 receives downlink telemetry from and sends uplink telemetry to an external programmer, as is conventional in implantable anti-arrhythmia devices, by means of an antenna 332. Data to be uplinked to the programmer and control signals for the telemetry circuit are provided by microprocessor 224 via address/data bus 218. EGM data that has been stored upon arrhythmia detection or as triggered by other monitoring algorithms may be uplinked to an external programmer using telemetry circuit 330. Received telemetry is provided to microprocessor 224 via multiplexer 220. Numerous types of telemetry systems known in the art for use in implantable devices may be used.

The remainder of the circuitry illustrated in FIG. 2 is an exemplary embodiment of circuitry dedicated to providing cardiac pacing, cardioversion and defibrillation therapies. The pacer timing and control circuitry 212 includes programmable digital counters which control the basic time intervals associated with various single, dual or multi-chamber pacing modes or anti-tachycardia pacing therapies delivered in the atria or ventricles. Pacer circuitry 212 also determines the amplitude of the cardiac pacing pulses under the control of microprocessor 224.

During pacing, escape interval counters within pacer timing and control circuitry 212 are reset upon sensing of R-waves or P-waves as indicated by signals on lines 202 and 206, respectively. In accordance with the selected mode of pacing, pacing pulses are generated by atrial pacer output circuit 214 and ventricular pacer output circuit 216. The pacer output circuits 214 and 216 are coupled to the desired electrodes for pacing via switch matrix 208. The escape interval counters are reset upon generation of pacing pulses, and thereby control the basic timing of cardiac pacing functions, including anti-tachycardia pacing.

The durations of the escape intervals are determined by microprocessor 224 via data/address bus 218. The value of the count present in the escape interval counters when reset by sensed R-waves or P-waves can be used to measure R-R intervals and P-P intervals for detecting the occurrence of a variety of arrhythmias.

The microprocessor 224 includes associated read-only memory (ROM) in which stored programs controlling the operation of the microprocessor 224 reside. A portion of the random access memory (RAM) 226 may be configured as a number of recirculating buffers capable of holding a series of measured intervals for analysis by the microprocessor 224 for predicting or diagnosing an arrhythmia.

In response to the detection of tachycardia, anti-tachycardia pacing therapy can be delivered by loading a regimen from microprocessor 224 into the pacer timing and control circuitry 212 according to the type of tachycardia detected. In the event that higher voltage cardioversion or defibrillation pulses are required, microprocessor 224 activates the cardioversion and defibrillation control circuitry 230 to initiate charging of the high voltage capacitors 246 and 248 via charging circuit 236 under the control of high voltage charging control line 240. The voltage on the high voltage capacitors is monitored via a voltage capacitor (VCAP) line 244, which is passed through the multiplexer 220. When the voltage reaches a predetermined value set by microprocessor 224, a logic signal is generated on the capacitor full (CF) line 254, terminating charging. The defibrillation or cardioversion pulse is delivered to the heart under the control of the pacer timing and control circuitry 212 by an output circuit 234 via a control bus 238. The output circuit 234 determines the electrodes used for delivering the cardioversion or defibrillation pulse and the pulse wave shape.

As discussed above, switch matrix 208 selects which of the various electrodes are coupled to band pass amplifier 210. Amplifier 210 may be a band-pass amplifier, having a band pass extending for approximately 2.5 to 100 hertz. The filtered EGM signal from amplifier 210 is passed through multiplexer 220, and digitized in A-D converter circuitry 222. The digitized EGM data is stored in random access memory 226 under control of direct memory address circuitry 228. Preferably, a portion of random access memory 226 is configured as a looping or buffer memory, which stores at least the preceding several seconds of the EGM signal.

The occurrence of an R-wave detect signal on line 202 is communicated to microprocessor 224 via data/address bus 218, and microprocessor 224 notes the time of its occurrence. If the morphology analysis function is activated, microprocessor 224 may, for example, wait 100 milliseconds or other physician selected interval following the occurrence of the R-wave detect signal, and thereafter transfer the most recent 200 milliseconds or other physician selected interval of digitized EGM stored in the looping or buffer memory portion of the random access memory circuit 226 to a second memory location, where the contents may be digitally analyzed according to the present invention. In this case, the transferred 200 milliseconds of stored EGM will correspond to a time window extending 100 milliseconds on either side of the R-wave detect signal. Window sizes in any case should be sufficient to allow analysis of the entire QRS complexes associated with the detected R-waves. The microprocessor also updates software-defined counters that hold information regarding the R-R intervals previously sensed. The counters are incremented on the occurrence of a measured R-R intervals falling within associated rate ranges. These rate ranges may be defined by the programming stored in the RAM 226

The following exemplary VT/VF detection method corresponds to that employed in commercially marketed Medtronic implantable pacemaker/cardioverter/defibrillators and employs rate/interval based timing criteria as a basic mechanism for detecting the presence of a tachyarrhythmia. To this end, the device defines a set of rate ranges and associated software-defined counters to track the numbers of intervals falling within the defined ranges.

A first rate range may define a minimum R-R interval used for fibrillation detection, referred to as "FDI". The associated VF count preferably indicates how many of a first predetermined number of the preceding R-R intervals were less than FDI.

A second rate range may include R-R intervals less than a lower tachycardia interval "TDI", and the associated VT count (VTEC) is incremented in response to an R-R interval less than TDI but greater then FDI, is not affected by R-R intervals less than FDI, and is reset in response to R-R intervals greater than TDI.

Optionally, the device may include a third rate range including R-R intervals greater than the FDI interval, but less than a fast tachycardia interval (FTDI) which is intermediate the lower tachycardia interval (TDI) and the lower fibrillation interval (FDI).

For purposes of the present example, the counts may be used to signal detection of an associated arrhythmia (ventricular fibrillation, fast ventricular tachycardia or lower rate ventricular tachycardia) when they individually or in combination reach a predetermined value, referred to herein as "NID's" (number of intervals required for detection). Each rate zone may have its own defined count and NID, for example "VFNID" for fibrillation detection and "VTNID"

for ventricular tachycardia detection or combined counts may be employed. These counts, along with other stored information reflective of the previous series of R-R intervals such as information regarding the rapidity of onset of the detected short R-R intervals, the stability of the detected R-R intervals, the duration of continued detection of short R-R intervals, the average R-R interval duration and information derived from analysis of stored EGM segments are used to determine whether tachyarrhythmia are present and to distinguish between different types of tachyarrhythmia. For purposes of illustrating the invention, an exemplary rate/interval based ventricular tachyarrhythmia detection method is described above. Other tachyarrhythmia detection methodologies, including detection methods as described in U.S. Pat. No. 5,991,656, issued to Olson, et al. on Nov. 23, 1999, U.S. Pat. No. 5,755,736, issued to Gillberg, et al. on May 26, 1998, both incorporated herein by reference in their entireties, or other known ventricular and/or atrial tachyarrhythmia detection methods may be substituted.

It is believed that the discrimination methods of the present invention may be usefully practiced in conjunction with virtually any underlying atrial or ventricular tachyarrhythmia detection scheme. Other exemplary detection schemes are described in U.S. Pat. No. 4,726,380, issued to Vollmann, U.S. Pat. No. 4,880,005, issued to Pless et al., U.S. Pat. No. 4,830,006, issued to Haluska et al., and U.S. patent application Ser. No. 09/566,477, filed May 8, 2000 by Gillberg et al., all incorporated by reference in their entireties herein. An additional set of tachycardia recognition methodologies is disclosed in the article "Onset and Stability for Ventricular Tachyarrhythmia Detection in an Implantable Pacer-Cardioverter-Defibrillator" by Olson et al., published in *Computers in Cardiology*, Oct. 7-10, 1986, IEEE Computer Society Press, pages 167-170, also incorporated by reference in its entirety herein. However, other criteria may also be measured and employed in conjunction with the present invention.

Figure 3:
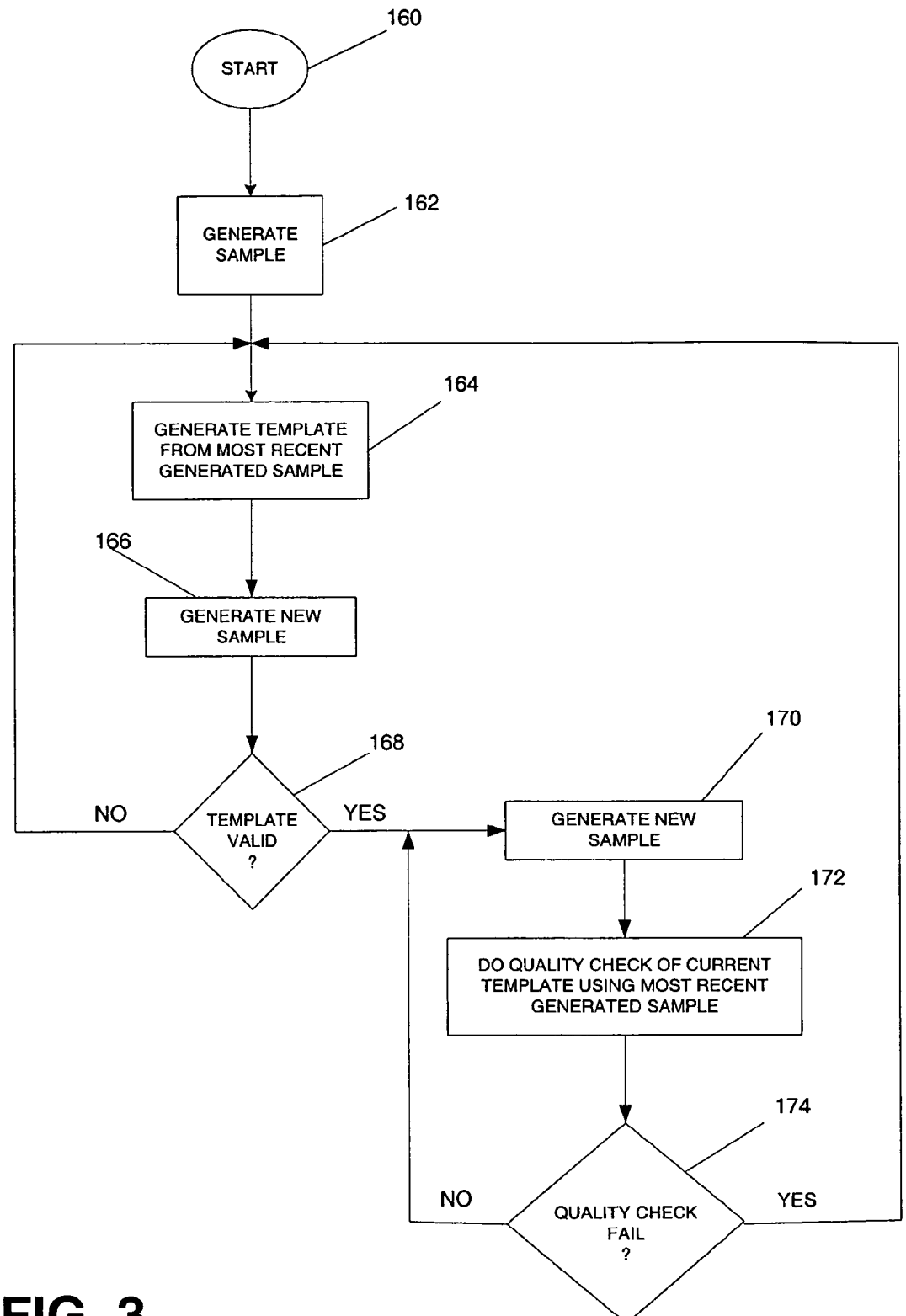
FIG. 3 is a flowchart of generation of a template for an implantable medical device according to an embodiment of the present invention.

FIG. 3 is a flowchart of generation of a template for an implantable medical device according to an embodiment of the present invention. As illustrated in FIG. 3, a template generation process according to the present invention includes a template generation portion, Blocks 162 and 164, a template validation portion, Blocks 166 and 168, and a template quality check portion, Blocks 170-174. Generation of a template according to the present invention is initiated by microprocessor 224, either automatically or manually at Block 160, using R-waves of the digitized EGM signals stored in random access memory 226. The generation of the template is initiated, for example, when no template currently exists, or upon recognition, either automatically by the implantable medical device, or manually by a physician, that the current template is no longer accurate, as will be described below. Once the automatic template generation process is initiated in Block 160, microprocessor 224 generates a sample of sensed beats, Block 162, from which a predetermined number of slow, non-paced beats are identified using a sample collection process described in detail below, and a template is then generated, Block 164, from the identified slow, non-paced beats.

Once the template is generated, microprocessor 224 generates another sample of sensed beats, Block 166, from which a predetermined number of slow, non-paced beats are identified and utilized to determine whether the current generated template is valid, Block 168. According to the present invention, if the template is determined to be invalid, microprocessor 224 generates a new template from the most recent generated sample, Block 164, i.e., the beats identified during validation of the template that was previously determined to be invalid, and the template validation portion, Blocks 166 and 168, is repeated to determine whether the new template is valid.

Once the template is determined to be valid, YES in Block 168, microprocessor 224 generates another sample of sensed beats, Block 170, from which a predetermined number of slow, non-paced beats are identified and utilized to perform a quality check of the most recent generated template, Block 172. If the template fails the quality check, YES in Block 174, microprocessor 224 generates a new template from the most recent generated sample, Block 164, i.e., the beats identified during the sample generation of Block 170, performed during the template quality check portion, and the template validation portion, Blocks 166 and 168, is repeated to determine whether the new template is valid.

If the quality check does not fail, NO in Block 174, microprocessor 224 generates another sample of sensed beats, Block 170, from which a predetermined number of slow, non-paced beats are identified and utilized to perform another quality check of the most recent generated template, Blocks 170-174. The template generation portion, Blocks 162 and 164, template validation portion, Blocks 166 and 168, and template quality check portion, Blocks 170-174 are all described below in detail.

As a result, when the template is determined to be invalid, either during the template validation portion, Blocks 166 and 168, or during the template quality check portion, Blocks 170-174, the template is updated using the most recently generated sample of sensed beats.

Figure 4:
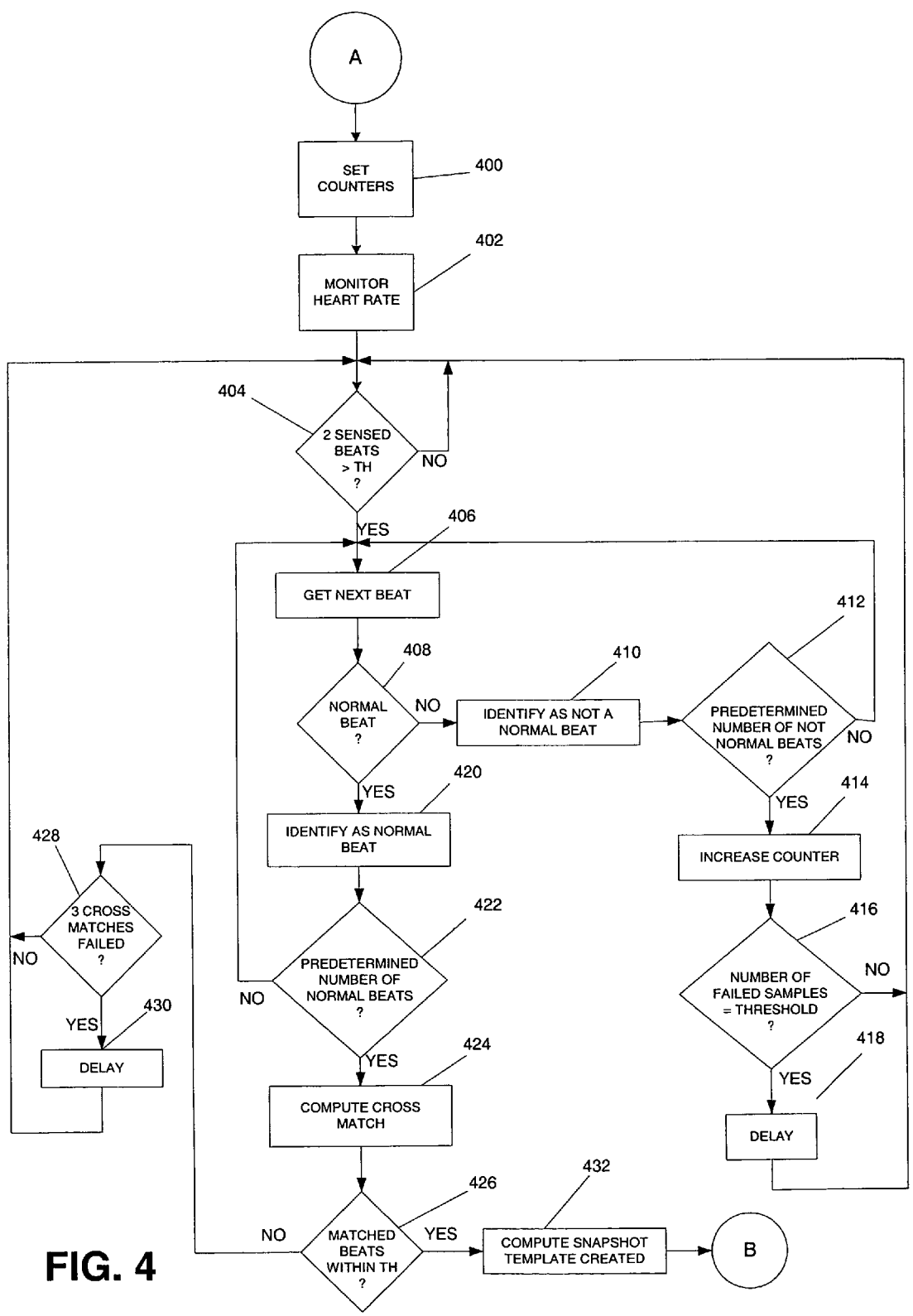
FIG. 4 is a flowchart of generation of a template for an implantable medical device according to an embodiment of the present invention.

FIG. 4 is a flowchart of generation of a template for an implantable medical device according to an embodiment of the present invention. As illustrated in FIGS. 2 and 4, a process for generation of a template according to the present invention is initiated by microprocessor 224, either automatically or manually, using R-waves of the digitized EGM signals stored in random access memory 226 at regular intervals. The template generation process is initiated, for example, when no template currently exists, or upon recognition, either automatically by the implantable medical device, or manually by a physician, that the current template is no longer accurate, as will be described below. Upon initiation of the automatic template generation process, microprocessor 224 sets counters corresponding to the number of beats collected, the normal beats collected, and the average R-wave to zero, Block 400 and begins monitoring the heart rate of the patient, Block 402.

According to the present invention, in order to maximize the probability of collecting slow, non-paced beats during the sample collection process, Blocks 404-422, from which to generate the template during the template generation process, Blocks 424-432, microprocessor 224 first determines whether two consecutive ventricular sensed (Vs) events having R-R intervals greater than a predetermined threshold have occurred, Block 404. The threshold utilized in Block 404 is programmable, and for example, is set as a given rate, such as 600 ms, or as a predetermined rate X above the lower tachycardia interval, TDI+X, with X being equal to 60 ms, for example, although the given rate or the predetermined rate X are programmable and therefore could be set at any desired value. In this way, by waiting until two consecutive, slow non-paced ventricular beats are identified, the present invention increases the likelihood that the desired series of slow, non-paced ventricular beats will be obtained and utilized to generate the template.

Once two consecutive ventricular sensed events having the predetermined rate corresponding to normal beats have been sensed, the next predetermined number of beats are classified as being either a beat corresponding to a normal beat or a beat corresponding to something other than a normal beat. According to an embodiment of the present invention, a beat is considered to be a normal beat if the sensed event is not a ventricular pace event, is a ventricular sense event having an R-R interval greater than a predetermined rate, such as 600 ms, for example, is not a first ventricular sense event to follow a ventricular pace event, or, if the beat is a ventricular sense beat that was immediately preceded by an atrial pace beat, the beat is a ventricular sense beat in which the interval between the ventricular sense beat and the prior atrial pace beat is greater than a predetermined threshold interval, such as 100 ms for example. The predetermined number of consecutive sensed events that are to be collected in is programmable, and according to an embodiment of the present invention, is set as twelve sensed beats, although any desired value could be utilized.

For example, as illustrated in FIG. 4, assuming the device is set so that an attempt is made to determine whether six out of the next twelve consecutive beats are normal beats, once two consecutive ventricular sensed events having the predetermined rate corresponding to normal beats have been sensed, YES in Block 404, a determination is made as to whether the next sensed beat, Block 406, is a normal beat, Block 408. According to an embodiment of the present invention, the sensed beat is determined not to be a normal beat, NO in Block 408, and is identified as not being a normal beat, Block 410, if the sensed beat is a paced beat, a sensed beat having an R-R interval less than 600 ms, a sensed beat that is the first sensed beat following a paced event, or, if the sensed beat was immediately preceded by a paced beat, the interval between the ventricular sensed beat and the prior atrial paced beat is less than or equal to 100 ms. A determination is then made as to whether a predetermined number of beats have been identified as not being normal beats, Block 412.

According to an embodiment of the present invention, in order to increase the likelihood that slow, non-paced beats will be utilized to generate the template, six of the twelve consecutive sensed beats must be identified as normal beats, although the present invention is not intended to be limited to six of twelve normal, and therefore any desired numbers may be utilized based on required system demands. Therefore, if it is determined that seven beats have been identified as not being normal beats, YES in Block 412, a failed sample counter C is incremented, and once the number of failed samples is equal to a predetermined threshold number, YES in Block 416, such as thirty for example, counter C is set equal to zero and the process is delayed for a predetermined time period, thereby reducing the likelihood that other than slow, non-paced beats will be utilized to generate the template. According to an embodiment of the present invention, the process is delayed for thirty-six minutes, Block 418, although any time period may be utilized. In addition, it is understood that while the threshold number corresponding to counter C is described as being thirty, any value desired value other than thirty could be utilized without departing from the present invention.

Once the delay period has expired, or if the number of failed samples is less than the predetermined threshold number, NO in Block 416, the process again waits until two consecutive beats having R-R intervals greater than the predetermined threshold have been sensed, Block 404, and the sample collection process, Blocks 404-422 is repeated. If the current beat has been identified as not being normal, but seven beats of the twelve consecutive beats have not yet been classified as not being normal, NO in Block 412, the next beat of the twelve consecutive beats is classified, Block 406, and the process is repeated using the next beat.

If it is determined that the current sensed beat is identified as a normal beat, YES in Block 408, i.e., the sensed beat is neither a paced beat, a sensed beat having an R-R interval less than 600 ms, a sensed beat that is the first sensed beat following a paced event, or, if the sensed beat was immediately preceded by an atrial pace beat, the interval between the ventricular sense beat and the prior atrial pace beat is less than or equal to 100 ms, the beat is identified as a normal beat, Block 420, and a determination is then made as to whether a predetermined number of beats have been identified as normal beats, Block 422. In the example where the predetermined number of consecutive beats is set as twelve, a determination is made as to whether six beats have been identified as being normal beats. If six beats have not been identified as being normal beats, NO in Block 422, the next beat of the twelve consecutive beats is classified, Block 406, and the process is repeated using the next beat.

Once the predetermined number of beats are identified as being normal beats, YES in Block 422, microprocessor 224 computes cross matches between the predetermined number of normal beats, Block 424. For example, according to the present invention, the first beat is matched against the second through sixth beats to generate five cross matches. A determination is then made as to whether a predetermined number of the computed cross matches are similar within a predetermined threshold, Block 426. For example, according to a preferred embodiment of the present invention, the predetermined threshold of Block 426 is normally 70% when known wavelet template matching algorithms are utilized and four of the five computed cross matches must be within the threshold, although any template matching algorithm or desired threshold values could be chosen without deviating from the present invention.

If the predetermined number of the computed cross matches are not similar within the predetermined threshold, a determination is made as to whether there have been a predetermined number of failed attempts at cross matching, Block 428, such as three for example. If there have been three failed attempts, YES in Block 428, the process is delayed for a predetermined period of time, such as two hundred and forty minutes, for example Block 430, although any time period may be utilized. Once the delay is completed in Block 430 or if it is determined that there have not been three failed attempts, NO in Block 428, the process returns to Block 404 and again waits until two consecutive beats having R-R intervals greater than the predetermined threshold have been sensed, and the sample collection process, Blocks 402-422 is repeated.

If the predetermined number of the computed cross matches are determined to be similar within the predetermined threshold, YES in Block 426, the predetermined number of cross matches that are similar within the predetermined threshold are averaged to create an average R wave snapshot, Block 432, that is then used as the current generated template.

Figure 5:
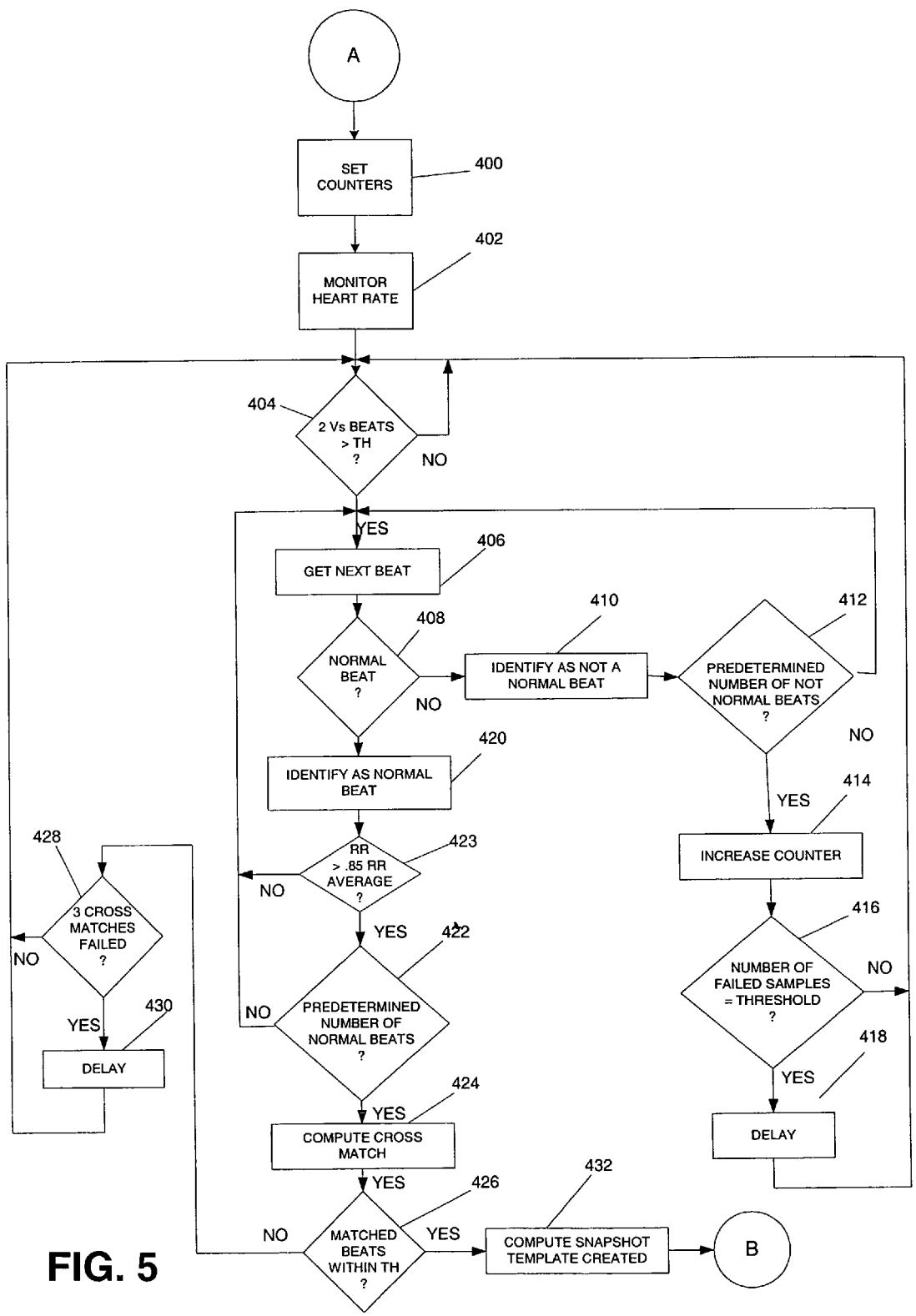
FIG. 5 is a flowchart of generation of a template for an implantable medical device according to an alternate embodiment of the present invention.

FIG. 5 is a flowchart of generation of a template for an implantable medical device according to an alternate embodiment of the present invention. According to an alternate embodiment of the present invention, the automatic template generation process is similar to the process described above in reference to FIG. 4, although an additional Block is included in the alternate embodiment to exclude premature ventricular contractions. In particular, as illustrated in FIG. 5, if the beat is identified as a normal beat, Block 420, a determination is made as to whether the R-R interval is greater than a predetermined average R-R interval, Block 423. In particular, according to a preferred embodiment of the present invention, a determination is made as to whether the R-R interval is greater than approximately 85% of the average R-R interval. However, it is understood that any percentage value could be chosen as long as the chosen percentage value serves to exclude premature ventricular contractions.

If it is determined in Block 423 that the R-R interval is not greater than 85% of the average R-R interval, i.e., the likelihood that the beat is representative of a premature ventricular contraction is great, the beat is excluded, and the process returns to Block 406 to monitor a next beat. On the other hand, if it is determined that the R-R interval is greater than 85% of the average interval, i.e., it is not likely that the beat is representative of a premature ventricular contraction, the process continues at Block 422 as described above in FIG. 4. Since the Blocks illustrated in FIG. 5, with the exception of Block 423, have previously been described above in reference to FIG. 4, description of the Blocks other than Block 423 has not been repeated merely for the sake of brevity.

While the present invention is described above as computing cross matches between beats once six beats have been collected, and determining whether four of the cross matches exceed the threshold, it is understood that the present invention is not limited to the use of six beats and four cross matches, but rather any number of beats and cross matches could be utilized, depending upon the particular patient or device requirements involved.

Figure 6:
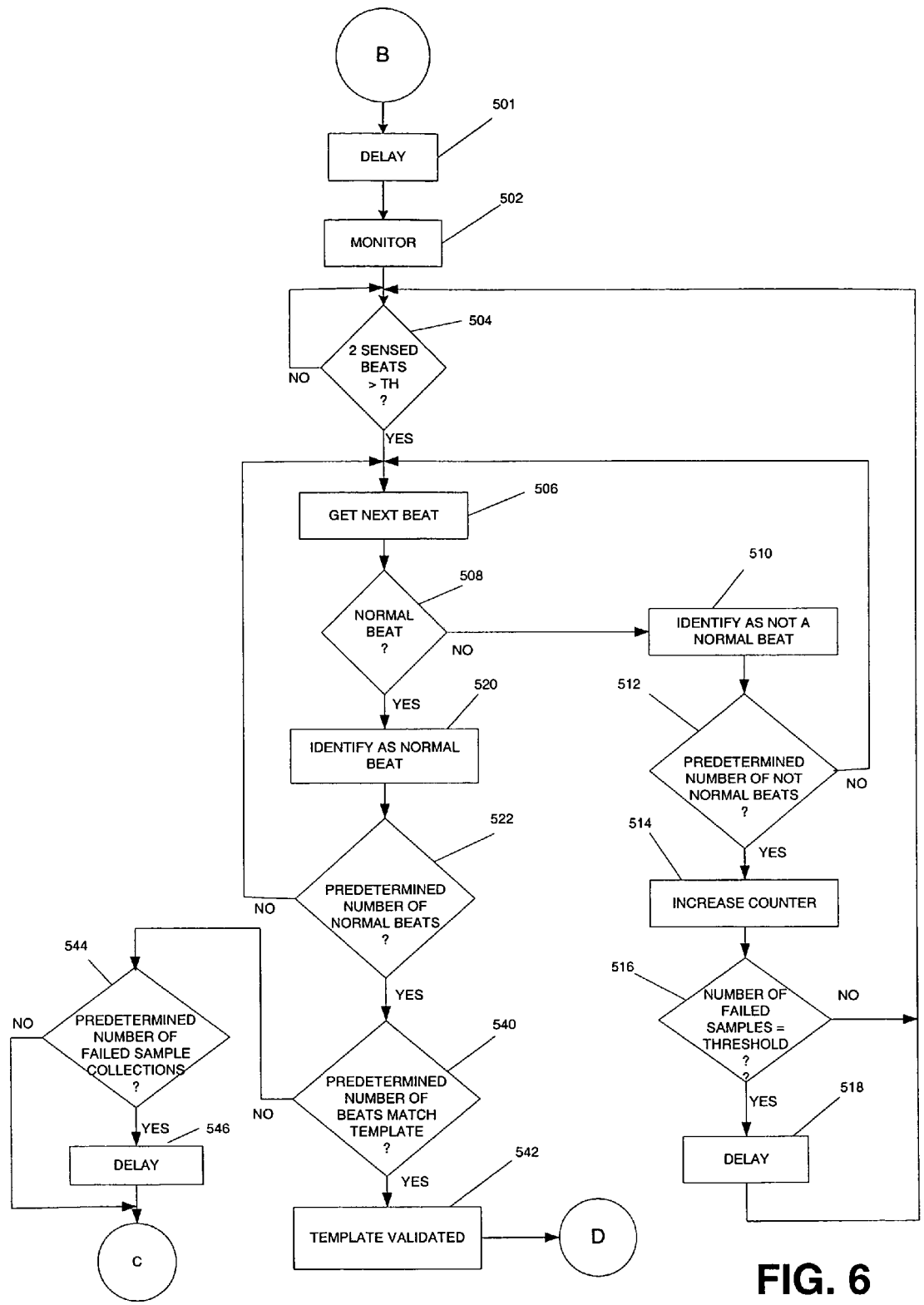
FIG. 6 is a flowchart of validation of a template for an implantable medical device according to an embodiment of the present invention.

FIG. 6 is a flowchart of validation of a template for an implantable medical device according to an embodiment of the present invention. According to the present invention, once the average R wave is created in the template generation stage described above for use as the template, the quality of the template is evaluated, based on matches between the template and ongoing slow heart rhythm. In particular, as illustrated in FIG. 6, the validation process is delayed for a predetermined time period, Block 500, such as fifteen minutes, for example, prior to initiating sample collection for validation of the template. Once the delay is completed, microprocessor 224 clears appropriate counters and, similar to the template generation process described above, determines whether two consecutive ventricular sensed (Vs) events having R-R intervals greater than a predetermined threshold have occurred, Block 504. The threshold utilized in Block 504 is programmable, and for example, is set as a given rate, such as 600 ms, or as a predetermined rate X above the lower tachycardia interval, TDI+X, with X being equal to 60 ms, for example, although the given rate or the predetermined rate X are programmable and therefore could be set at any desired value.

Assuming again that the device is programmed so that an attempt is made to determine whether six of the next twelve consecutive beats are normal beats, once two consecutive ventricular sensed events having the predetermined rate corresponding to normal beats have been sensed, YES in Block 504, a determination is made as to whether the next sensed beat, Block 506, is identified as being a normal beat, Block 508. As described above, the sensed beat is determined not to be a normal beat, NO in Block 508, and is identified as not being a normal beat, Block 510, if the sensed beat is a paced beat, a sensed beat having an R-R interval less than 600 ms, a sensed beat that is the first sensed beat following a paced event, or, if the sensed beat was immediately preceded by an atrial pace beat, the interval between the ventricular sense beat and the prior atrial pace beat is less than or equal to 100 ms. Once the beat is identified as not being a normal beat, a determination is then made as to whether a predetermined number of beats of the predetermined number of consecutive beats have been identified as not being normal beats, Block 512.

For example, as described above, if it is determined that seven beats are not normal beats, YES in Block 512, a failed sample counter C is incremented, Block 514, and once the number of failed samples is equal to a predetermined number, YES in Block 516, such as thirty, for example, counter C is set equal to zero and the process is delayed for a predetermined time period, Block 518, thereby reducing the likelihood that other than slow, non-paced beats will be utilized to validate the template. According to an embodiment of the present invention, the process is delayed for thirty-six minutes, Block 518, although any time period may be utilized. In addition, it is understood that while the threshold number corresponding to counter C is described as being thirty, any value desired value other than thirty could be utilized without departing from the present invention.

Once the delay period has expired, or if the number of failed samples is less than the predetermined threshold number, NO in Block 516, the process again waits until two consecutive beats having R-R intervals greater than the predetermined threshold have again been sensed, Block 504 and the sample collection process, Blocks 504-522 is repeated. If the current beat has been identified as not being a normal beat, but less than a predetermined number beats of the predetermined number of consecutive beats, such as less than seven of twelve beats, for example, have been identified as not being normal beats, NO in Block 512, the next beat of the twelve consecutive beats is classified, Block 506, and the process is repeated using the next beat.

If it is determined that the current sensed beat is a normal beat, YES in Block 508, i.e., the sensed beat is neither a paced beat, a sensed beat having an R-R interval less than 600 ms, a sensed beat that is the first sensed beat following a paced event, or, if the sensed beat was immediately preceded by an atrial pace beat, the interval between the ventricular sense beat and the prior atrial pace beat is greater than 100 ms, the beat is identified as being a normal beat, Block 520, a determination is then made as to whether a predetermined number of beats have been identified as being normal beats, Block 522. In the example where the predetermined number of consecutive beats is set as twelve, the determination in Block 522 is whether six beats have been identified as being normal beats. If the predetermined number of normal beats have not been collected, NO in Block 522, the next beat of the twelve consecutive beats is classified, Block 506, and the process is repeated for the next beat.

According to the present invention, once the predetermined number of normal beats are identified during the template validation process, YES in Block 522, a determination is then made for each of the predetermined number of beats as to whether a predetermined number of the normal beats from the current sample collection match the generated template within a predetermined threshold, Block 540. For example, according to the present invention, a determination is made as to how many of the beats match the template within a predetermined threshold, such as approximately 70%, for example. However, the threshold is not limited to this value, and could be programmed as determined by a physician. If a predetermined number of the collected beats match the template within the threshold, such as four out of the six matched beats, for example, the template is validated, Block 542. However, if four out of six of the beats do not match the template within the threshold, a failed sample collection match counter is incremented and a determination is made as to whether a predetermined number of sample collections have failed to match the template, Block 544, such as two, for example. If there have been the predetermined number of sample collections that have failed to match the template, YES in Block 544, the process is delayed for a predetermined delay period, such as approximately two hundred and forty minutes, for example, Block 546, although any time period may be utilized. Once the delay is completed in Block 546 or if it is determined that there have been less than the predetermined number of sample collections that have failed to match the template, NO in Block 544, the template is updated, Block C, using the normal beats resulting from the sample collection performed during the template validation process, Blocks 502-524 of FIG. 6.

Figure 7:
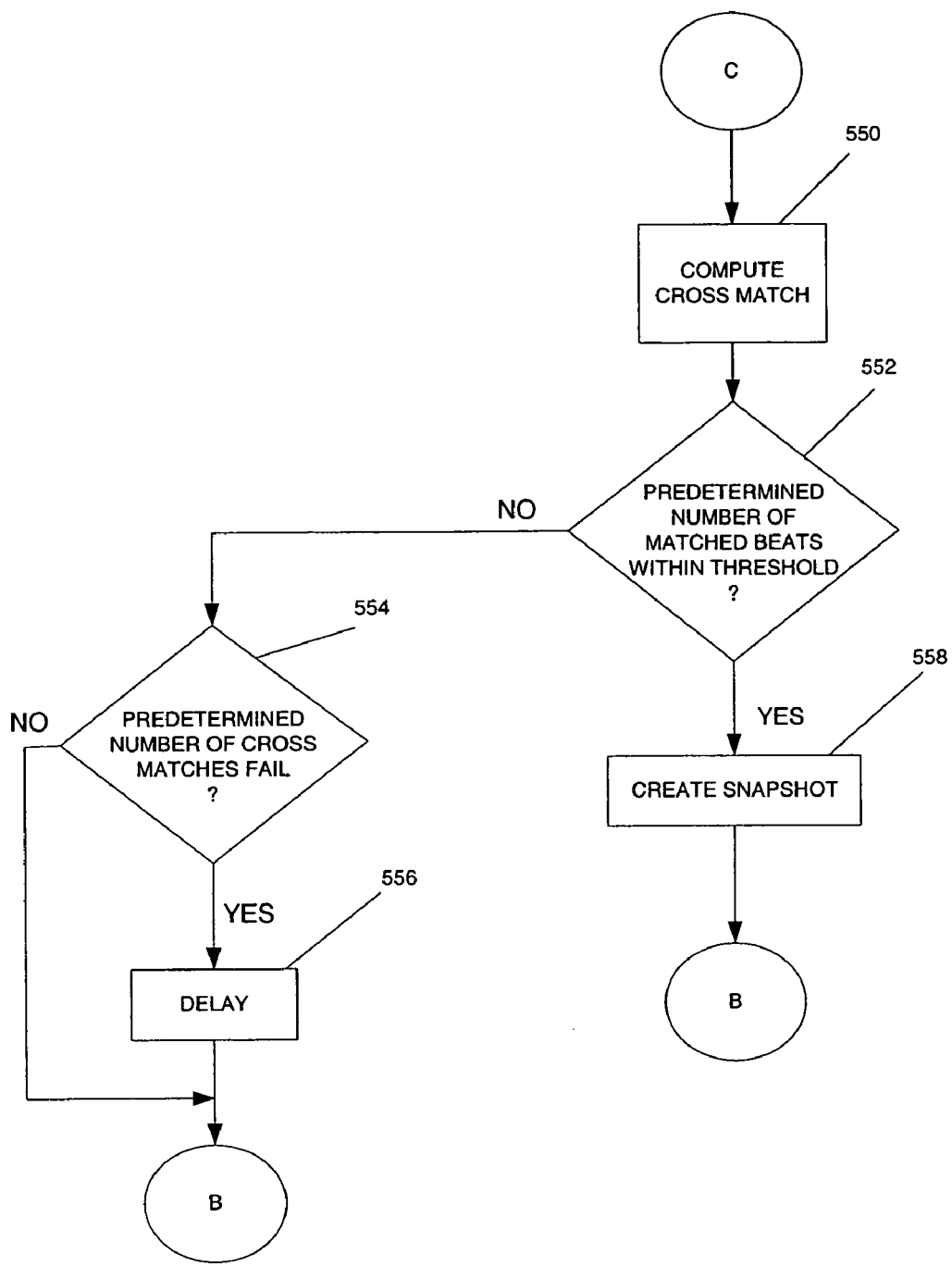
FIG. 7 is a flowchart of updating of a template during a template validation process in an implantable medical device according to an embodiment of the present invention.

FIG. 7 is a flowchart of updating of a template during a template validation process in an implantable medical device according to an embodiment of the present invention. As illustrated in FIG. 7, once the delay, Block 546, is completed during the validation process, or if it is determined that there have been less than the predetermined number of sample collections that have failed to match the template, NO in Block 544, the current template is updated, Block C, by first computing cross matches, Block 550, between the predetermined number of matched beats resulting from the sample collection performed during the template validation process, Blocks 502-522 of FIG. 6, with the first beat being matched against the second through sixth beats to generate five cross matches. A determination is then made as to whether a predetermined number of the computed cross matches are similar within a predetermined threshold, Block 552. For example, as described above, the predetermined threshold of Block 552 is nominally 70% and four of the five computed cross matches must be within the threshold, although any desired values could be chosen without deviating from the present invention.

If the predetermined number of the computed cross matches are not similar within the predetermined threshold, a determination is made as to whether there have been a predetermined number of failed attempts at cross matching, Block 554, such as three for example. If there have been the predetermined number of failed attempts, YES in Block 554, the process is delayed for a predetermined period of time, Block 556, such as two hundred and forty minutes, for example, although any time period may be utilized. Once the delay is completed in Block 556 or if it is determined that there have not been the predetermined number of failed attempts, NO in Block 554, the sample collection portion of the template validation process, Blocks 502-522, is repeated until new matched beats are generated, YES in Block 522, and the determination of whether the predetermined number of beats match the current template, Blocks 540-546, is repeated using the most recently generated matched beats.

If the predetermined number of the computed cross matches are determined to be similar within the predetermined threshold, YES in Block 552, the predetermined number of cross matches that are similar within the predetermined threshold are averaged to create an average R wave snapshot, Block 558, that is then used as the updated template. The sample collection portion of the template validation process, Blocks 502-522, is then repeated until new matched beats are generated, YES in Block 522, and the determination of whether the predetermined number of beats match the updated template, Blocks 540-546, is repeated using the newly generated matched beats.

Figure 8:
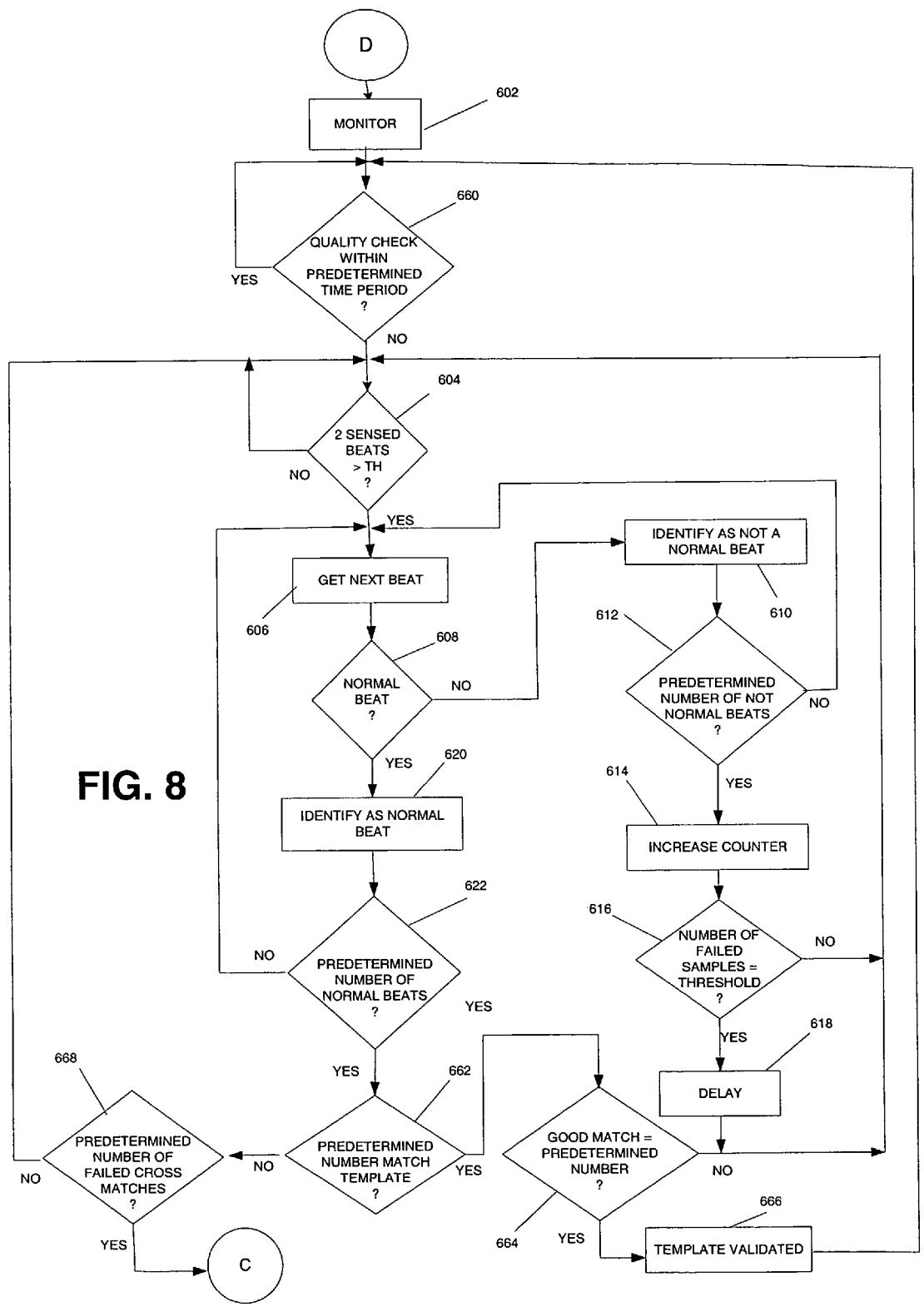
FIG. 8 is a flow chart of a quality check of a template in an implantable medical device according to an embodiment of the present invention.

FIG. 8 is a flow chart of a quality check of a template in an implantable medical device according to an embodiment of the present invention. As illustrated in FIGS. 6 and 8, once it is determined during validation of the template that the predetermined number of the collected beats match the template within the threshold, such as four out of the six good beats, for example, and therefore the template is validated, Block 542 of FIG. 6, the template quality check is initiated and a determination is made as to whether a quality check has been performed within a predetermined time period, Block 660, such as three hours for example. Once it is determined that the quality check has not been performed for the predetermined time period, NO in Block 660, microprocessor 224 clears appropriate counters and, similar to both the template generation and validation processes described above, begins a sample collection process by determining whether two consecutive ventricular sensed (Vs) events having R-R intervals greater than a predetermined threshold have occurred, Block 604.

Assuming again that the device is programmed so that an attempt is made to determine whether six of the next twelve consecutive beats are normal beats, once two consecutive ventricular sensed events having the predetermined rate corresponding to normal beats have been sensed, YES in Block 604, a determination is made as to whether the next sensed beat, Block 606, is identified as being a normal beat, Block 608. As described above, the sensed beat is determined not to be a normal beat, NO in Block 608, and is identified as not being a normal beat, Block 610, if the sensed beat is a paced beat, a sensed beat having an R-R interval less than 600 ms, a sensed beat that is the first sensed beat following a paced event, or, if the sensed beat was immediately preceded by an atrial pace beat, the interval between the ventricular sense beat and the prior atrial pace beat is less than or equal to 100 ms. Once the beat is identified as not being a normal beat, a determination is then made as to whether a predetermined number of beats of the predetermined number of consecutive beats have been identified as not being normal beats, Block 612, such as seven beats, for example, when the predetermined number of consecutive beats is equal to twelve beats.

For example, as described above, if it is determined that the predetermined number of beats are not normal beats, YES in Block 612, a failed sample counter C is incremented, Block 614, and once the number of failed samples is equal to a predetermined number, YES in Block 616, such as thirty, for example, counter C is set equal to zero and the process is delayed for a predetermined time period, Block 618, thereby reducing the likelihood that other than slow, non-paced beats will be utilized to perform the quality check of the template. According to an embodiment of the present invention, the process is delayed for thirty-six minutes, Block 618, although any time period may be utilized. In addition, it is understood that while the threshold number corresponding to counter C is described as being thirty, any value desired value other than thirty could be utilized without departing from the present invention.

Once the delay period has expired, or if the number of failed samples is less than the predetermined threshold number, NO in Block 616, the process again waits until two consecutive beats having R-R intervals greater than the predetermined threshold have again been sensed, Block 604, and the sample collection process, Blocks 604-622 is repeated. If the current beat has been identified as not being a normal beat, but less than a predetermined number beats of the predetermined number of consecutive beats, such as less than seven of twelve beats, for example, have been identified as not being normal, NO in Block 612, the next beat of the twelve consecutive beats is classified, Block 606, and the process is repeated using the next beat.

If it is determined that the current sensed beat is a normal beat, YES in Block 608, i.e., the current sensed beat is not a paced beat, is a sensed beat having an R-R interval greater than a predetermined rate, such as 600 ms for example, is not a first sensed event following a paced event, or, if the current sensed event was immediately preceded by an atrial pace event, the interval between the ventricular sense event and the prior atrial pace event is greater than 100 ms, the beat is identified as being a normal beat, Block 620, a determination is then made as to whether a predetermined number of beats have been identified as being normal beats, Block 622. In the example where the predetermined number of consecutive beats is set as twelve, the determination in Block 622 is whether six beats have been identified as being normal beats. If the predetermined number of normal beats have not been collected, NO in Block 622, the next beat of the twelve consecutive beats is classified, Block 606, and the process is repeated for the next beat.

According to the present invention, once the predetermined number of normal beats are identified during the template quality check process, YES in Block 622, a determination is made as to whether a predetermined number of the newly generated normal beats resulting from the current sample collection process, Blocks 604-622, match the current template within a predetermined threshold, Block 662. For example, according to the present invention, if the predetermined number of normal beats in Block 622 is six beats, a determination is made in Block 662 as whether four out of the six beats match the template within a predetermined threshold, such as approximately 70%, for example. However, the threshold is not limited to this value, and could be programmed as determined by a physician.

If the predetermined number out of the collected beats match the template within the threshold, i.e., four out of six beats, the sample collection is considered to be a good template match, and therefore a template match counter is incremented and a determination is made as to whether there have been a predetermined number of sample collections generated during the sample collection process, Blocks 604-622, such as four for example, that have been determined to be good template matches, i.e., samples having four of six beats that match the template, Block 664. If there have not been the predetermined number of sample collections resulting in good template matches, NO in Block 664, another sample collection is generated, Blocks 604-622, and the quality check portion, Blocks 660-668 is repeated for the newly generated sample collection. If there have been the predetermined number of sample collections resulting in good template matches, the template quality has been validated, Block 666, and the quality check process is repeated after the three hour delay, Block 660.

If the predetermined number out of the collected beats do not match the template within the threshold, NO in Block 662, the sample collection is considered to be a bad template match, and therefore a template bad match counter is incremented and a determination is made as to whether there have been a predetermined number of samples collections generated during the sample collection process, Blocks 604-622, such as three for example, that have been determined to be bad template matches, Block 668. If there have not been the predetermined number of bad template matches, NO in Block 668, another sample collection is generated, Blocks 604-622, and the quality check portion, Blocks 660-668 is repeated for the newly generated sample collection.

If there have been the predetermined number of bad template matches, YES in Block 668, the template quality check has failed, and therefore the template is updated, Block C (FIG. 7) using beats resulting from the most recent sample collection generated during the template quality check process, Blocks 604-622, and the template validation process and the template quality process are repeated.

Some of the techniques described above may be embodied as a computer-readable medium comprising instructions for a programmable processor such as microprocessor 224 or control circuitry 212 shown in FIG. 2. The programmable processor may include one or more individual processors, which may act independently or in concert. A "computer-readable medium" includes but is not limited to any type of computer memory such as floppy disks, conventional hard disks, CR-ROMS, Flash ROMS, nonvolatile ROMS, RAM and a magnetic or optical storage medium. The medium may include instructions for causing a processor to perform any of the features described above for initiating a session of the escape rate variation according to the present invention.

The preceding specific embodiments are illustrative of the practice of the invention. It is to be understood, therefore, that other expedients known to those of skill in the art or disclosed herein may be employed without departing from the invention or the scope of the appended claim. It is therefore to be understood that the invention may be practiced otherwise than as specifically described, without departing from the scope of the present invention. As to every element, it may be replaced by any one of infinite equivalent alternatives, only some of which are disclosed in the specification.

What is claimed is:

1. A method of generating a template of a normal heartbeat of a heart of a patient, comprising:
    detecting heartbeats as a plurality of events;
    collecting a predetermined number of detected non-paced heartbeats having predetermined characteristics during a first discrete sample collection interval and identifying them as first selected events;
    generating a current template from the collected first selected events;
    waiting a predetermined delay;
    collecting a predetermined number of detected non-paced heartbeats having predetermined characteristics during a second discrete sample collection interval subsequent to the first discrete sample collection interval and the predetermined delay and identifying the predetermined number of detected non-paced heartbeats collected during the second discrete sample collection interval as second selected events; then
    comparing the collected second selected events with the current template to obtain a result; and
    generating an updated template from the collected second selected events in response to the result being an invalid template; and
    delivering a therapy to the heart of the patient based, at least in part, on the updated template.

2. The method of claim 1, further comprising:
    identifying events of the plurality of events having the predetermined characteristics as third selected events;
    monitoring the template in response to the third selected events; and
    updating the template using the third selected events in response to the monitoring.

3. The method of claim 1, wherein identifying events as first selected events and identifying events as second selected events comprises:
    determining whether there are consecutive events of the plurality of events having first characteristics; and
    identifying a predetermined number of events of the plurality of events subsequent to the consecutive events having second characteristics as one of first selected events and second selected events.

4. The method of claim 3, wherein the first characteristics correspond to two consecutive events that are ventricular sensed events having RR-intervals greater than a threshold interval.

5. The method of claim 3, wherein the second characteristics include a ventricular sense event other than a ventricular pace event, a ventricular sense event having an R-R interval greater than a predetermined rate, a ventricular sense event other than a first ventricular sense event immediately following a ventricular pace event, and a ventricular sense event that was immediately preceded by an atrial pace event and for which an interval between the ventricular sense event and the atrial pace event is greater than a threshold interval.

6. The method of claim 5, wherein the predetermined rate is approximately equal to 600 ms and the threshold interval is approximately equal to 100 ms.

7. The method of claim 3, further comprising:
computing a cross-match between the predetermined number of events identified as first selected events to generate cross-matches; and
determining whether a predetermined number of the generated cross-matches are within a predetermined cross-match threshold, wherein the template is generated from events of the predetermined number of events corresponding to the cross-matches determined to be within the cross-match threshold.

8. The method of claim 7, further comprising:
determining, in response to the predetermined number of the generated cross-matches not being within a predetermined cross-match threshold, whether a predetermined number of cross-match computations have failed to generate the predetermined number of generated cross-matches that are within the predetermined cross-match threshold; and
generating a delay in response to the predetermined number of cross-match computations having failed to generate the predetermined number of generated cross-matches that are within the predetermined cross-match threshold.

9. The method of claim 3, further comprising:
determining whether RR-intervals associated with the first selected events are greater than an average RR-interval;
computing, in response to the RR-intervals associated with first selected events being greater than an average RR-interval, a cross-match between the predetermined number of events identified as first selected events to generate cross-matches; and
determining whether a predetermined number of the generated cross-matches are within a predetermined cross-match threshold, wherein the template is generated from events of the predetermined number of events corresponding to the cross-matches determined to be within the cross-match threshold.

10. The method of claim 1, further comprising:
determining whether there are consecutive events during the first and second discrete sample collection intervals having first characteristics; and
identifying a predetermined number of events of the plurality of events subsequent to the consecutive events having second characteristics;
wherein the first characteristics correspond to two consecutive events that are ventricular sensed events having RR-intervals greater than a threshold interval, and the second characteristics include a ventricular sense event other than a ventricular pace event, a ventricular sense event having an R-R interval greater than a predetermined rate, a ventricular sense event other than a first ventricular sense event immediately following a ventricular pace event, and a ventricular sense event that was immediately preceded by an atrial pace event and for which an interval between the ventricular sense event and the atrial pace event is greater than a threshold interval.

11. An implantable medical device, comprising:
means for detecting heartbeats as a plurality of sensed events;
means for collecting a predetermined number of detected non-paced heartbeats having predetermined characteristics during a first discrete sample collection interval and identifying them as first selected events;
means for generating a current template from the collected first selected events;
means for waiting a predetermined delay;
means for collecting a predetermined number of detected non-paced heartbeats having predetermined characteristics during a second discrete sample collection interval subsequent to the first discrete sample collection interval and the predetermined delay and identifying the predetermined number of detected non-paced heartbeats collected during the second discrete sample collection interval as second selected events;
means for comparing the collected second selected events with the current template to obtain a result after the collection of the second selected events; and
means for generating an updated template from the collected second selected events in response to the result being an invalid template.

12. The device of claim 11, further comprising:
means for identifying events of the plurality of events having the predetermined characteristics as third selected events;
means for monitoring the template in response to the third selected events; and
means for updating the template using the third selected events in response to the monitoring.

13. The device of claim 11, wherein the means for identifying events as first selected events and the means for identifying events as second selected events comprise:
means for determining whether there are first consecutive events of the plurality of events having first characteristics; and
means for identifying a predetermined number of events of the plurality of events subsequent to the first consecutive events having second characteristics as first selected events.

14. The device of claim 13, wherein the first characteristics correspond to two consecutive events that are ventricular sensed events having RR-intervals greater than a threshold interval.

15. The device of claim 13, wherein the second characteristics include being a ventricular sense event other than a ventricular pace event, a ventricular sense event having an R-R interval greater than a predetermined rate, a ventricular sense event other than a first ventricular sense event immediately following a ventricular pace event, and a ventricular sense event that was immediately preceded by an atrial pace event and for which an interval between the ventricular sense event and the atrial pace event is greater than a threshold interval.

16. The device of claim 15, wherein the predetermined rate is approximately equal to 600 ms and the threshold interval is approximately equal to 100 ms.

17. The device of claim 13, further comprising:
means for computing a cross-match between the predetermined number of events identified as first selected events to generate cross-matches; and
means for determining whether a predetermined number of the generated cross-matches are within a predetermined cross-match threshold, wherein the template is generated from events of the predetermined number of events corresponding to the cross-matches determined to be within the cross-match threshold.

18. The device of claim 17, further comprising:
means for determining, in response to the predetermined number of the generated cross-matches not being within a predetermined cross-match threshold, whether a predetermined number of cross-match computations have failed to generate the predetermined number of generated cross-matches that are within the predetermined cross-match threshold; and
means for generating a delay in response to the predetermined number of cross-match computations having failed to generate the predetermined number of generated cross-matches that are within the predetermined cross-match threshold.

19. The device of claim 13, further comprising:
means for determining whether RR-intervals associated with the first selected events are greater than an average RR-interval;
means for computing, in response to the RR-intervals associated with first selected events being greater than an average RR-interval, a cross-match between the predetermined number of events identified as first selected events to generate cross-matches; and
means for determining whether a predetermined number of the generated cross-matches are within a predetermined cross-match threshold, wherein the template is generated from events of the predetermined number of events corresponding to the cross-matches determined to be within the cross-match threshold.

* * * * *